United States Patent [19]

Balakrishnan

[11] Patent Number: 4,982,334
[45] Date of Patent: Jan. 1, 1991

[54] CALENDER CONTROL SYSTEM FOR SHEETMAKING

[75] Inventor: Ramesh Balakrishnan, Stanford, Calif.

[73] Assignee: Measurex Corporation, Cupertino, Calif.

[21] Appl. No.: 303,481

[22] Filed: Jan. 27, 1989

[51] Int. Cl.$^5$ ............................................. G06F 15/46
[52] U.S. Cl. .................................. 364/469; 162/252; 162/DIG. 10; 364/471; 364/572
[58] Field of Search ............... 364/469, 552, 554, 568, 364/575, 576, 572, 471, 724.12, 724.18, 728.01, 725, 726, 148, 152; 162/252, 253, 258, 262, 263, DIG. 6, DIG. 10; 100/43, 48, 50, 99, 161, 162 R, 162 B, 163 R, 163 A

[56] References Cited

U.S. PATENT DOCUMENTS

| | | | |
|---|---|---|---|
| 3,496,344 | 2/1970 | Chope | 364/554 |
| 3,557,351 | 1/1971 | Doering | 364/560 X |
| 4,453,404 | 6/1984 | Powell et al. | 364/471 X |
| 4,648,712 | 3/1987 | Brenholdt | 356/432 X |
| 4,674,045 | 6/1987 | Kerber et al. | 364/413.21 X |
| 4,707,779 | 11/1987 | Hu | 364/469 |
| 4,791,863 | 12/1988 | Vahatalo | 100/162 B X |

Primary Examiner—Joseph Ruggiero
Attorney, Agent, or Firm—Burns, Doane, Swecker & Mathis

[57] ABSTRACT

A system for controlling the calendering of sheet materials includes means for receiving measurements of one property of sheet material during production wherein the input to the system represents the setpoints of a calender profile actuator system. In operation, the system first calculates a linear trend line from a pattern of setpoints. Then, the linear trend line is substrated from the pattern of setpoints and used to control an edge loading system. The residual setpoints are provided to a frequency splitter whose low frequency output is used to determine the setpoints of a crown roll system and whose high frequency output is used to determine the setpoints of a calender profile actuator system.

18 Claims, 3 Drawing Sheets

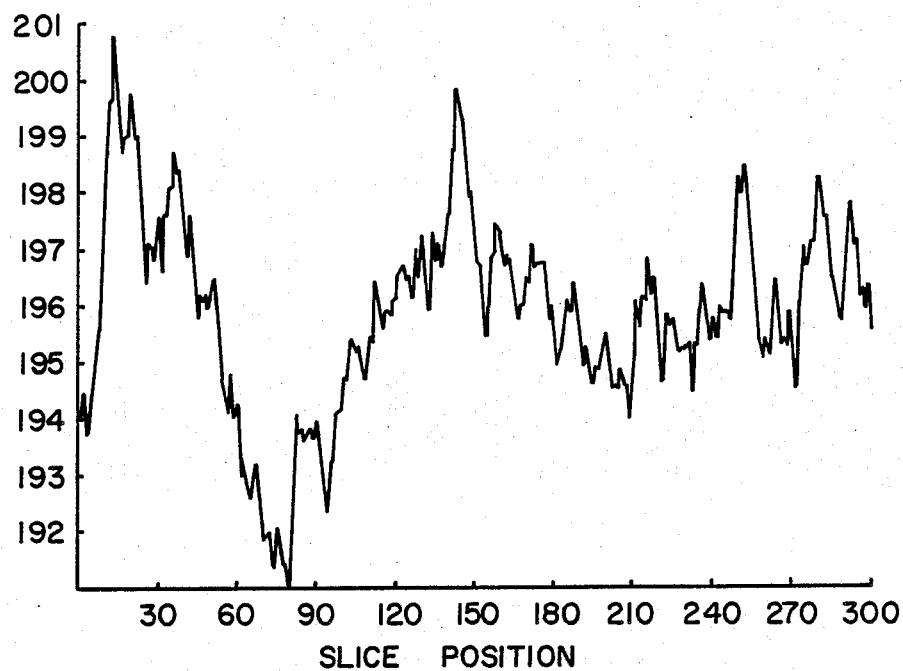
FIG._1.
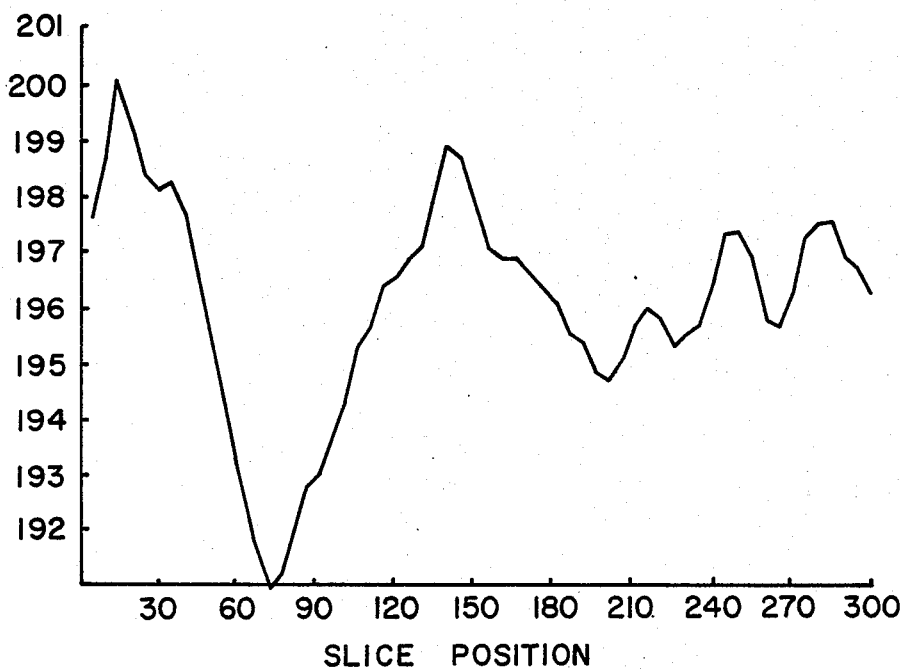
FIG._2.

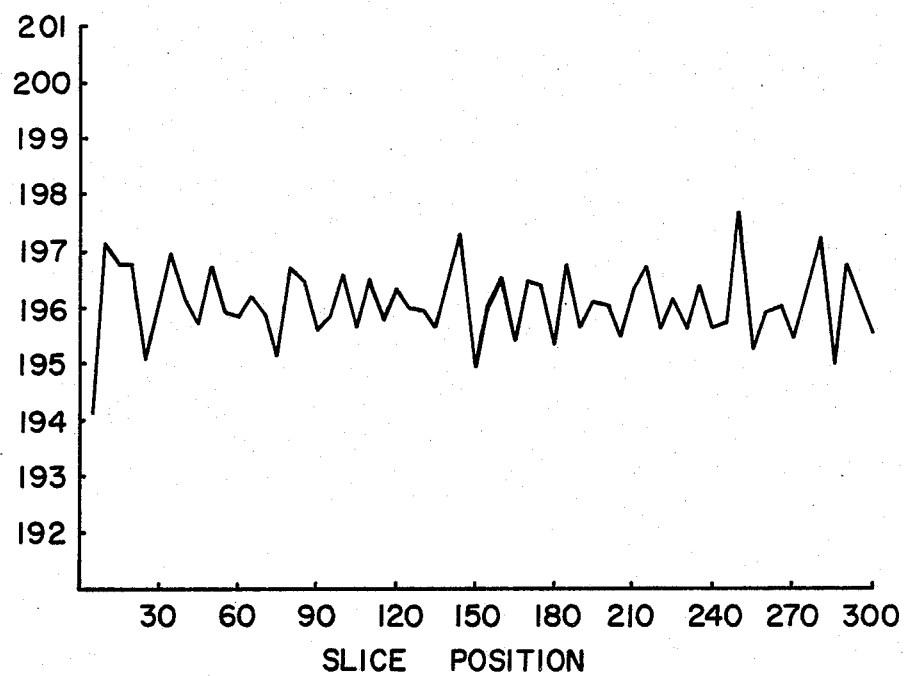
FIG._3.

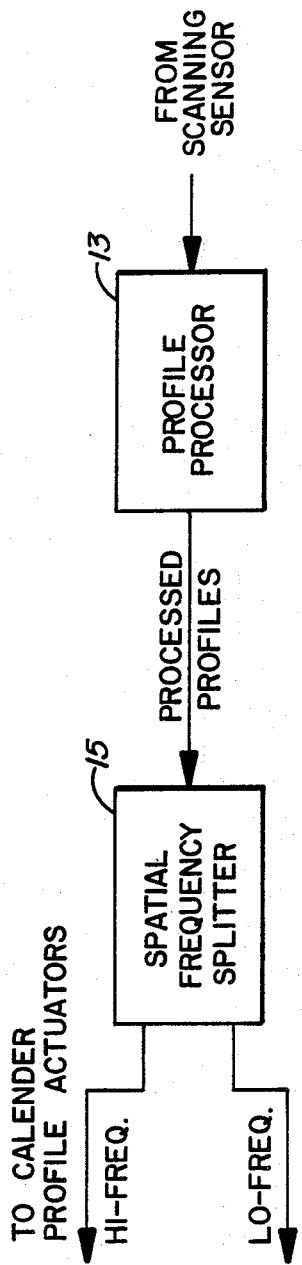
FIG._4.
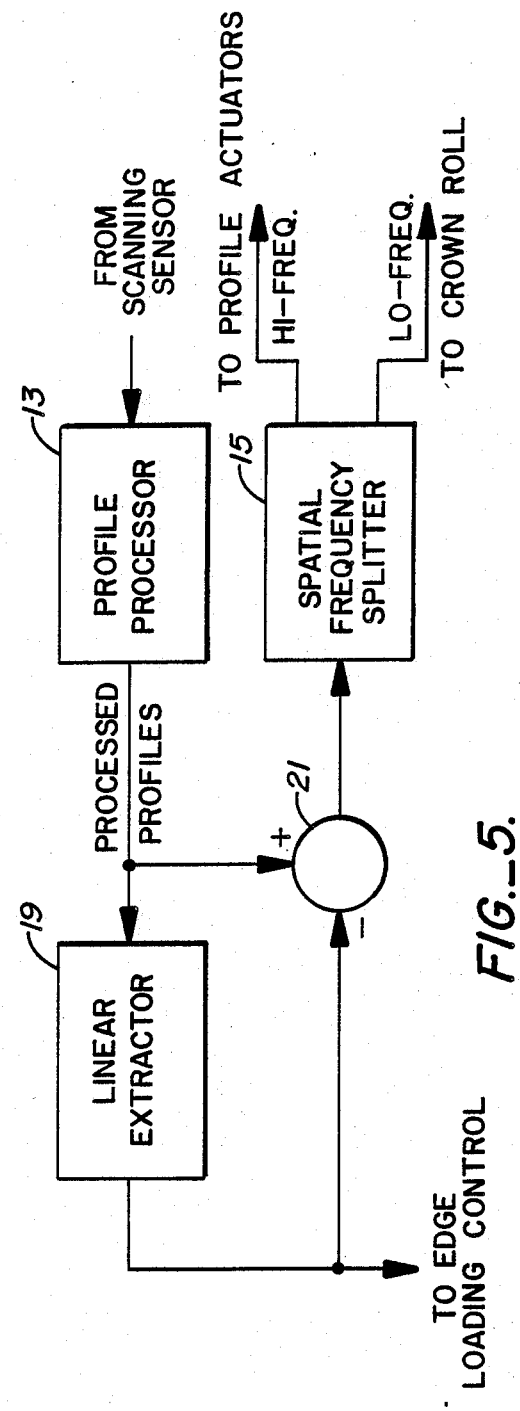
FIG._5.

CALENDER CONTROL SYSTEM FOR SHEETMAKING

BACKGROUND OF THE INVENTION

1. Field of the Invention

The present invention generally relates to systems for controlling sheetmaking machines and, more particularly, to systems for the control of calendering systems that employ multiple actuators.

2. Related Art

In the sheetmaking art, it is common practice to make on-line measurements of sheet properties. The purpose of on-line measurements is to enable prompt control of sheetmaking processes and, thus, to increase sheet uniformity and to reduce the quantity of substandard sheet material that is produced before undesirable process conditions are corrected. In papermaking, for instance, it is well known to employ on-line sensors that detect sheet properties such as basis weight, moisture content, and caliper.

It is well known that on-line measurements can be made by sensors that periodically traverse, or "scan", traveling sheets in the cross direction, i.e., in a direction extending across the sheet surface generally perpendicular to the direction of sheet travel. In practice, scanning sensors typically travel at a rate of about ten inches per second and provide an integrated output about every fifty milliseconds; thus, a typical scanning sensor provides about one measurement output per each half-inch in the cross direction. Measurement information detected by scanning sensors is often assembled to provide graphlike "profiles" composed of successions of measurements at adjacent locations, or "slices", in the cross direction. Cross-directional profiles also can be provided by measurement systems that employ arrays of fixed sensors that extend in the cross direction to simultaneously measure a sheet property at a plurality of slice locations.

To control sheetprocessing machines to produce uniform quality sheets, it is common practice to detect variations that occur both between and within cross-directional profiles. In the machine direction (i.e., the direction of sheet travel), sheet uniformity can be defined as the condition where the average value of a measured sheet property is constant from profile to profile; thus, machine-directional uniformity generally implies that cross-directional profiles do not change from scan to scan. In the cross direction, sheet uniformity can be defined as a measured sheet property being constant from slice to slice; thus, cross-directional sheet uniformity implies flat profiles.

Various devices are known to control sheet properties. In papermaking, for instance, a property known as "caliper" (i.e., sheet thickness) can be controlled by calendering and supercalendering machines In modern sheetmaking operations, a typical calendering or supercalendering machine comprises a series of rolls arranged in parallel, one above the other, in a "stack". The sheet material is then trained through the stack to pass through the nip areas between adjacent rolls. The effect of calendering and supercalendering is to change the caliper of sheet materials In calendering and supercalendering machines, two of the basic parameters that can be continuously controlled are nip pressure and roll temperature. The two properties are interdependent, however, because an increase in temperature of a metal roll will cause it to physically expand, thereby increasing compressional pressure on sheet material at the nip area.

In practice, various actuators can control calendering pressure on calendering and supercalendering machines. For example, it is known to use edge loading devices that control the pressure loading on the ends of the rolls of a calender stack. Also, it is known to use crown rolls. Generally speaking, a crown roll contains an internal hydraulic mechanism which exerts hydraulic pressure to change the curvature laterally along a roll. In practice, the hydraulic mechanisms can either cause the lateral surface of a crown roll to have a convex, flat, or a concave shape. Also in practice, it is known to employ so-called sectionalized crown rolls. Those devices are divided lengthwise into zones, each of which can be controlled independently as a crown roll.

Also, the pressure exerted by calendering and supercalendering machines can be controlled by calender profile actuators. Those devices operate to heat calender rolls differentially along their lengths. In systems that employ calender profile actuators, the caliper of a sheet is detected at selected cross-directional locations following the calendering machine, and then selected sections, or "zones", of certain ones of the calender rolls are heated or cooled based upon the detected caliper.

One example of a system for controlling calender rolls is shown in U.S. Pat. No. 4,573,402. In the system described in the patent, sensors are provided to monitor hardness and uniformity of a reel during a reel-building process subsequent to calendering. Then, based upon the monitored values, actuators act upon the calender rolls to cause changes in their temperature and, hence, to change their diameters in a manner which adjusts paper hardness and uniformity. In particular, the patent describes a system wherein the actuators direct air through heating elements to reach selected sections of the calender rolls; also, the patent states that localized cooling of the calender rolls can be achieved by directing ambient air through ones of the heating elements that are not energized.

Another example of a calender control system is described in U.S. Pat. No. 4,114,528. In the system described in the patent, a paper web, after leaving a series of calender rolls, passes through a scanning device that generally continuously detects web-thickness information across the width of the web. According to the patent, the calender rolls are heated or cooled in response to detected differences in thickness of the paper web with the goal of achieving constant web thickness. More particularly, the patent states that air, either from a hot air plenum or from a cold air plenum, is selectively directed against individual longitudinal sections of the calender rolls in response to detected variations from normal thickness of the produced paper web.

Yet another example of a calender control system is set forth in U.S. Pat. No. 4,384,514. According to that patent, thermally-induced changes in nip clearance between calender rolls are achieved by devices that generate electromagnetic fields that interact with the metal of the rolls to provide induction heating at selected locations along the lengths of the rolls. The patent further suggest that sections of the rolls can be insulated from one another to localize the induction heating effects. In addition, the patent states that temperature increases at selected sections of the calender rolls can be controlled by auxiliary air or liquid cooling systems.

Also, U.S. Pat. No. 4,685,389 describes a calender profile actuator system. According to the patent, a plurality of nozzles are located at preselected locations along a plenum which extends the length of a calender roll. The nozzles each contain an individually controllable heating element for selectively heating the flow of air through the associated nozzles. The temperature of air ejected from the nozzles, in turn, controls the diameter of the calender roll and directly affects the thickness of calendered sheet material. A calender profile actuator system substantially as described in the patent has been commercialized by Measurex Corporation of Cupertino, Calif., and is known as the Caltrol control system. In that system, the caliper profile control actuators include devices which control high velocity air jets to impinge upon a calender roll over a temperature range from ambient (80° F.) to 650° F. In practice, the air flow from each jet is on half-slice centers.

In practice, calender profile actuator systems normally have relatively narrow control zones and relatively fast response times and, therefore, are well suited for correction of narrow (e.g. 0 to 300 mm.), short-term profile variations. However, actual caliper profiles often exhibit wider and more stable fluctuations, such as full-width slants, bowl shapes and s-curves. Conventional calender actuator profile systems are not well-suited for correcting such profile variations. Instead, wide and stable fluctuations in caliper profiles can be better corrected by edge loading devices or by crown rolls of the sectionalized or non-sectionalized type.

A difficulty in using profile measurements for cross-directional control of sheet properties arises when a sheetprocessing machine, such as a calender stack, employs two or more profiling systems that are both capable of affecting the same property of sheet material. In such situations, the control issue is one of deciding how the various profiling systems should be controlled when the control signals, at any given time, are derived from the same cross-direction profile. For example, in the case of a calendering stack controlled by both a calender profile actuator system and a sectionalized crown roll, the control issue would be one of deciding how the control signals are to be distributed between the calender profile actuator system and the sectionalized crown roll.

In conventional control practice, multiple control systems on the same sheetmaking machines are often operated with actuating signals distributed, at any given time, according to a predetermined ratio. Such practice is often referred to as "ratioing" of signals. Another conventional strategy for operating two or more profile control systems on a sheetprocessing machines is called "mid-ranging". In a typical mid-ranging strategy, a first profile control system is operated as long as the set points of its actuators fall within predetermined limits, i.e., within a defined "mid-range". When one or more of the set points moves outside the preselected mid-range, the second profile control system is actuated. Normally, the limits for the mid-ranges are selected based upon prior operating experience and upon the capabilities of the actuators in the control systems.

At this juncture, it should be appreciated that conventional control strategies, such as ratioing and midranging, do not necessarily result in optimum use of the profile control system which is best suited to make adjustments to overcome detected non-uniformities in sheet profiles.

In U.S. patent applications Ser. No. 207,412, filed June 15, 1988, and commonly assigned herewith, the disclosure of which is herein incorporated by reference, there is disclosed a method and system for controlling two or more profiling systems which control the same property of sheet material which is being produced. The system described in the application employs control signals obtained from scanners that measure a given property of a sheet at numerous locations to provide cross-directional profiles. More specifically, the system described in the application employs a spatial-frequency splitting technique for separating, for each cross-directional profile, low spatial-frequency components from high spatial-frequency components. Then, the separated high and low spatial-frequency components are used to provide operating signals to control two or more profiling systems to modify properties of produced sheet material.

BRIEF DESCRIPTION OF THE DRAWINGS

FIG. 1 is a graph depicting a typical profile comprised of successive measurements of a sheet property in the cross direction of a travelling sheet;

FIG. 2 is a graph depicting the low spatial-frequency components of the profile of FIG. 1;

FIG. 3 is a graph depicting the high spatial-frequency components of the graph of FIG. 1;

FIG. 4 is a generalized block diagram of a control system for use in a system according to the present invention; and FIG. 5 is a functional diagram of a more detailed embodiment of the system shown as in FIG. 4.

DETAILED DESCRIPTION OF THE PREFERRED EMBODIMENT

FIG. 1 shows an example of a cross-directional profile provided by a measurement system which measures the caliper of a sheet at successive cross-directional locations. Values along the vertical axis in FIG. 1 indicate the magnitude of caliper along a given scan, and the values on the horizontal axis indicate the cross-directional location, or slice, at which the caliper is measured. Thus, for example, the depicted caliper profile has a value of about 197 at the 120th slice. (If the scanned sheet is 300 inches wide and is divided, for instance, into 300 equal slices of one-inch width, the 120th slice in the graph of FIG. 1 would be one hundred twenty inches from one edge of the sheet.)

Under ideal sheetmaking conditions, measured caliper would be constant along each profile and each of the caliper actuators would be operating relatively close to its mid-range. Thus, the profile shown in FIG. 1 indicates that the caliper of the sheet deviates substantially from the ideal cross-directional uniformity.

At this juncture, it should be noted that control conditions are not necessarily ideal even if a caliper profile is flat. The control conditions would be defined as non-ideal if some of the caliper control devices were operating relatively close to their upper or lower ranges to maintain the flat profile. With the control devices operating at or near full range, the caliper control devices might not be able to respond to changes in profile measurements while remaining within their operating ranges.

By analyzing the caliper profile in FIG. 1 in terms of its spatial frequency (measured in terms of cycles per unit distance in the cross direction), the profile can be found to have low-frequency sinusoidal components as well as substantial high-frequency components, including noise. Thus, FIGS. 2 and 3 show the low and high spatial-frequency components, respectively, of the caliper profile of FIG. 1. It may be noted that the profile magnitudes in FIGS. 2 and 3 can be summed, at each slice location, to provide the profile in FIG. 1.

In the following, the process of separating high and low frequency components of a cross-directional profile will be referred to as "spatial-frequency splitting". This term is chosen to emphasize the distinction between spatial-frequency signals and time-domain signals.

FIG. 4 illustrates the basic components of a system for controlling two or more profiling devices on a calendering machine based upon a strategy of spatial-frequency splitting. The illustrated system, which is referred to herein as a multifrequency actuator control system, includes a profile processor 13 and a spatial-frequency splitter 15. In the preferred embodiment, the inputs to the system are from a conventional scanning sensor which measures the caliper of a sheet at a plurality of consecutive cross-directional locations comprising a scan. It should be understood that profile processor 13 is a conventional signal processor such as the mini-slice (TM) processor available from Measurex Corporation of Cupertino, Calif. The output of profile processor 13 will be referred to herein as processed profiles. If desired, the output signals from the profile processor be assembled over each scan to display cross-directional caliper profiles.

In operation of the multi-frequency actuator control system of FIG. 4, spatial-frequency splitter 15 functions to decompose the processed profile measurements into low and high spatial-frequency components as illustrated by FIGS. 2 and 3. Spatial-frequency splitter 15 is normally operated at a tuning factor greater than unity so that the low frequency output comprises spatial-frequency components having periods exceeding the tuning factor. As shown, the low frequency output signals from frequency splitter 15 are provided to a control system for one or more crown rolls, and the high frequency output signals are provided to a caliper profile actuator system such as the Measurex Caltrol system.

As is explained in the above-identified co-pending application, spatial-frequency splitter 15 of FIG. 4 can produce a desired separation of frequencies by smoothing or convolution techniques In the case of convolution, a cross-directional profile is convolved with a function which produces an output having the desired frequency spectra characteristics. The convolving function is sometimes referred to as a "window" function. When a cross-directional profile is convolved with a suitable window function, the resulting profile will display substantially unaltered components of the original profile having spatial-frequencies less than a preselected "cutoff" frequency, but components having spatial-frequencies exceeding the cutoff frequency will be substantially attenuated (i.e., diminished in magnitude). As an example of a suitable window function, the co-pending application discloses a function of the type known as a Blackman function. The disclosed Blackman function had generally constant amplitude over a range of low frequencies and then rapidly decreased to zero at frequencies near a selected cutoff frequency.

As is also explained in the co-pending application, the cutoff spatial-frequency can be expressed as a so-called "tuning" factor which, mathematically, is inversely related to the cutoff frequency. Accordingly, for a selected tuning factor, spatial-frequency splitter 15 of FIG. 4 operates to attenuate spatial-frequency components of a cross-directional profile having periods shorter than the tuning factor but generally will not alter spatial-frequency components having periods longer than the tuning factor. Thus, for relatively large tuning factors, the spatial-frequency splitter 15 of FIG. 4 will attenuate all but relatively low spatial frequencies. In practice of the present invention, a tuning factor is selected based upon the actuator zone width and the cross-directional response characteristics of a given calender profile actuator system. For a typical such system having an actuator zone width of about ten inches and response characteristic of about twenty inches per zone, a suitable tuning factor would be about two slice widths per cycle or, equivalently, about twenty inches per cycle.

FIG. 5 illustrates a more detailed example of a multifrequency actuator control system. Following profile processor 13, the system of FIG. 5 includes a linear extractor 19 and a summer 21. At summer 21, the output of linear extractor 19 is subtracted from the output of profile processor 13. Therefore, the output of summer 21 comprises components of processed profiles from which certain components have been subtracted or "extracted". Further in the system of FIG. 5, the output of summer 21 is connected to the input of spatial frequency splitter 15.

Operation of the multi-frequency actuator control system of FIG. 5 will now be described for situations where profile processor 13 computes simple arithmetical averages of profile signals according to the widths of actuator zones of a given calender profile actuator systems. For example, for a calender profile actuator system having one hundred independent actuator zones of equal width extending across a four-hundred inch sheet, profile processor 13 would compute simple arithmetical averages for profile measurements every four inches. In practice, the calculations performed by profile processor 13 can also reflect the extent of coupling between actuator zones.

Further in operation of the multi-frequency actuator control system of FIG. 5, linear extractor 19 operates to calculate a stack-wide straight line profile from the processed profile information. The straight line profile is, in essence, a linear trend line which is computed by linear regression using measurement values from slice to slice across a profile. THe extracted straight line profile is then provided to control an edge loading system. This control allows adjustment of the edge loading system to reduce caliper profile slant while maintaining average caliper.

As an example of typical practice in accordance with the system of FIG. 5, it can be assumed that three profiling systems are available at a calendering machine: a calender profile actuator system, an edge loading system and a crown roll system. For a given full-width caliper profile (i.e., a profile across a sheet from edge-to-edge), a stack-wide straight line profile is extracted by extractor 19 as previously described to control an edge loading system. Then spatial frequency splitter 15 operates upon the residual profile to separate it into component profiles whose spatial frequencies correspond to the control zone widths of the crown rolls used on the given calendering machine. For non-sectionalized crown rolls, the control zone width is approximately half the calender stack width. For sectionalized crown rolls, the control zone width is generally inversely proportional to the number of sections. For instance, for a sectionalized crown roll with four sections across a calendering machine, the control zone width would be approximately one-eighth of the calender stack width; likewise, for a sectionalized crown roll with six sections, the control zone width would be approximately one-twelfth of the calender stack width. Finally, as shown in FIG. 5, the high spatial-frequency profiles are provided to control calendar profile actuators, such as the Measurex Caltrol actuators, having relatively narrow control zones and relatively fast response times.

The primary benefit of the above-described system is that it increases the range of caliper control while reducing cross-directional caliper control variations. The increase in control range is due to the fact that low spatial-frequency signals are separately used in controlling profiling devices having low spatial-frequency response characteristics (i.e., crown rolls) while the high spatial-frequency signals are used for controlling those profiling devices having high spatial-frequency response characteristics.

The system of FIG. 5 can also be employed in situations where the input to the system represents the setpoints of a calender profile actuator system. In that case, the system operates to first calculate a linear trend line from the setpoint pattern. Then the linear trend line is subtracted from the pattern of setpoints and used to control an edge loading system. The residual setpoints are provided to the frequency splitter 15, whose low frequency output is used to determine the setpoints of a crown roll system and whose high frequency output is used to determine the setpoints of a calender profile actuator system. Such usage of the system allows the setpoints of the caliper profile actuators to be brought toward values which are more in the mid-range of the actuators. As so adjusted, the caliper profile actuators are then able to respond to profile variations which, otherwise, would be beyond the range of the actuators.

Although preferred embodiments of methods and systems according to the present invention have been described, those skilled in the art will appreciate that additions, modifications, substitutions and deletions not specifically described in the foregoing may be made without departing from the spirit and scope of the present invention as defined by the following claims.

What is claimed is:

1. A system for controlling the calendering of sheet materials, comprising:
    means for receiving inputs that represent the setpoints of a calender profile actuator system;
    spatial-frequency splitting means for operating upon the received inputs to separate relatively high spatial-frequency components from relatively low spatial-frequency components;
    means to provide control signals to a crown roll based upon the relatively low spatial-frequency components; and
    means to provide control signals to a caliper profile actuator system based upon relatively high spatial-frequency components.

2. A system according to claim 1 wherein the spatial-frequency splitting means separates high spatial-frequencies from low spatial-frequencies for each set of setpoints.

3. A system according to claim 1 wherein the setpoints are caliper profile actuator setpoins.

4. A system according to claim 3 wherein the crown roll is a segmented crown roll.

5. A system for controlling the calendering of sheet materials, comprising:
    means for receiving caliper measurements during the calendering of sheet material, which measurements are made at a plurality of cross-directional locations that successively span the sheet material;
    means for computing a linear trend of the received caliper measurements;
    means to provide the linear trend to control an edge loading device;
    means for subtracting the linear trend from the received measurements to, thereby, provide residual cross-directional caliper profile measurements;
    spatial-frequency splitting means for operating upon the residual cross-directional caliper profile measurements to separate relatively high-frequency spatial-frequency components from relatively low spatial-frequency components;
    means to provide control signals to a segmented crown roll based upon the relatively low spatial-frequency components; and
    means to provide control signals to a caliper profile actuator system based upon the relatively high spatial-frequency components.

6. A system according to claim 5 wherein the spatial-frequency splitting means separates high spatial-frequencies from low spatial-frequencies for each cross-directional profile.

7. A system according to claim 5 wherein the measurements are caliper measurements.

8. A system according to claim 5 wherein the spatial-frequency splitting means separates high spatial-frequencies from low spatial-frequencies by convolution.

9. A process for providing control signals to systems that adjust the calendering of sheet materials during production, comprising the steps of:
    measuring the caliper of traveling sheet material at a plurality of cross-directional locations by scanning the sheet material;
    for the measurements, determining a set of setpoints of a calender profile actuator system;
    separating the relatively high spatial-frequency components of the set of setpoints from the relatively low spatial-frequency components;
    controlling a crown roll based upon the low spatial-frequency components; and
    controlling a caliper profile actuator system based upon the relatively high spatial-frequency components.

10. A process according to claim 9 wherein the high spatial-frequencies are separated from low spatial-frequencies by convolution.

11. A process according to claim 10 wherein the convolution is accomplished by convolving cross-direction profiles with a Blackman-type function.

12. A process for providing control signals to systems that adjust the calendering of sheet materials during production, comprising the steps of:
    measuring the caliper of traveling sheet material at a plurality of cross-directional locations by scanning the sheet material;
    for the measurements taken along each scan determining a linear trend line;
    controlling an edge loading device based upon the linear trend line;

for each scan, extracting the linear trend line from the caliper profile measurements to provide residual caliper measurements;

for the residual caliper measurements for each scan, separating the relatively high spatial-frequency components of the measurements from the relatively low spatial-frequency components;

controlling a crown roll based upon the low spatial-frequency components; and controlling a caliper profile actuator system based upon the relatively high spatial-frequency components.

13. A system for controlling the calendering of sheet material, comprising:

means for receiving signals which represent the set points of at least one profiling system which controls the calendering of sheet material;

spatial-frequency splitting means for operating upon the received setpoint signals to separate relatively high spatial-frequency components of the signals from relatively low spatial-frequency components;

means to provide control signals for one profile system based upon the relatively low spatial-frequency components; and means to provide control signals for at least one other profiling system based upon the relatively high spatial-frequency components.

14. A system according to claim 13 wherein the spatial-frequency splitting means separates high spatial-frequency components from low spatial-frequency components for each cross-directional profile.

15. A system according to claim 13 wherein said one profiling system controls the caliper of sheet material.

16. A system according to claim 13 wherein said one profiling system is a segmented crown roll.

17. A system for controlling the calendering of sheet materials during production, comprising:

means for receiving signals which represent the set points of at least one profiling system which controls the calendering of sheet material;

means for computing linear trend information of the received setpoint signals;

means to provide the linear trend information to control an edge loading device;

means for subtracting the linear trend information from the setpoint signals to, thereby, provide residual cross-directional setpoint information;

spatial-frequency splitting means for operating upon the residual setpoint information to separate relatively high-frequency spatial-frequency components from relatively low spatial-frequency components;

means to provide control signals to a segmented crown roll system based upon the relatively low spatial-frequency components; and means to provide control signals to a caliper profile actuator system based upon the relatively high spatial-frequency components.

18. A system according to claim 17 wherein the spatial-frequency splitting means separates high spatial-frequency components from low spatial-frequency components by convolution.

* * * * *